United States Patent [19]

Muto et al.

[11] Patent Number: 5,089,481
[45] Date of Patent: Feb. 18, 1992

[54] POLYSACCHARIDES AND ANTIVIRAL DRUGS CONTAINING THE SAME AS ACTIVE INGREDIENT

[75] Inventors: Shigeaki Muto, Tokyo; Koichi Niimura, Sayama; Minoru Oohara, Tokyo; Yoshiharu Oguchi, Tokyo; Kenichi Matsunaga, Tokorozawa; Kunitaka Hirose, Tokyo; Junji Kakuchi, Tokyo; Norifumi Sugita, Tokyo; Takao Furusho, Tokyo; Chikao Yoshikumi, Tokyo; Masaaki Takahashi, Tokyo, all of Japan

[73] Assignee: Kureha Kagaku Kogyo Kabushiki Kaisha, Tokyo, Japan

[21] Appl. No.: 613,971

[22] Filed: Nov. 15, 1990

Related U.S. Application Data

[63] Continuation of Ser. No. 207,835, Jun. 17, 1988, abandoned.

[30] Foreign Application Priority Data

Jun. 18, 1987 [JP] Japan .............................. 62-152086
Jun. 18, 1987 [JP] Japan .............................. 62-152087
Jun. 18, 1987 [JP] Japan .............................. 62-152089

[51] Int. Cl.$^5$ .................... A61K 31/70; C08B 37/00
[52] U.S. Cl. ..................................... 514/54; 536/1.1; 536/123; 424/88; 424/92; 514/885

[58] Field of Search ............... 536/1.1, 123; 514/53, 514/54, 885; 424/88, 92, 95

[56] References Cited

U.S. PATENT DOCUMENTS

| | | | |
|---|---|---|---|
| 4,663,438 | 5/1987 | Yoshikumi et al. | 530/395 |
| 4,699,787 | 10/1987 | Ueno et al. | 424/95 |
| 4,746,511 | 5/1988 | Kobatake et al. | 536/1.1 |
| 4,761,402 | 8/1988 | Williams | 514/54 |
| 4,831,020 | 5/1989 | Watanabe et al. | 536/123 |

FOREIGN PATENT DOCUMENTS

0209078 11/1987 European Pat. Off. .

OTHER PUBLICATIONS

*Journal of Cancer Research and Clinical Oncology*, vol. 113, No. 5, 1987, pp. 413–416, Nakanishi et al., "Antiretroviral Activity in a Marine . . . ".
Patent Abstracts of Japan, vol. 7, No. 235 (C-191), 19 Oct. 1983.
Hirose, Biochem Biophys Res Comm (12/1987), 149(2):562–567.

*Primary Examiner*—Ronald W. Griffin
*Attorney, Agent, or Firm*—Nixon & Vanderhye

[57] ABSTRACT

Disclosed herein are polysaccharides extracted from marine algae and an antiviral drug containing as active ingredient polysaccharides extracted from seaweeds.

14 Claims, No Drawings

POLYSACCHARIDES AND ANTIVIRAL DRUGS CONTAINING THE SAME AS ACTIVE INGREDIENT

This is a continuation of application Ser. No. 07/207,835, filed June 17, 1988, now abandoned.

BACKGROUND OF THE INVENTION

The present invention relates to polysaccharides obtained from marine algae, particularly algae belonging to the classes Phaeophyceae, Rhodophyceae and Chlorophyceae, and the antiviral drugs, particularly antiretroviral drugs, more particularly anti-AIDS viral drugs, containing the polysaccharides as active ingredient. The "polysaccharides" referred to in the present invention means a polysaccharide and a protein-bound polysaccharide.

In recent years a new type of irremediable diseases such as AIDS (acquired immunodeficiency syndrome) has been attracted, and the development of therapeutic agents for this disease has been strongly desired. Presently, a nucleic acid derivative called 3'-azido-3'-deoxy thymidine (AZT) is known as the only available therapeutic agent for AIDS. As for the cause of this disease, it has already been disclosed by many researchers that a human immunodeficiency virus (HIV), which is a sort of retrovirus, is adsorbed on a human $T_4$ lymphocyte to infect this lymphocyte and other lymphocyte one after another until finally the immune system is destroyed.

The present inventors had already found many protein-bound polysaccharides which can serve as a biological resoponse modifier (BRM) for the immune system. For example, they had proposed the following polysaccharides having an anticancer activity in British Patent No. 1,331,513.

Polysaccharides obtained from a liquid extract of a mycelium of a fungus species of Basidiomycetes or from a cultured broth of said species, said polysaccharides being free or substantially free of impurities originally present in said liquid extract or in said cultured broth, and being characterized by being a water-soluble amorphous solid which is non-hydroscopic and non-dialyzable; gives a positive result when tested for the presence of glucose after hydrolysis with 1N sulphuric acid; gives negative results when subjected to the ferric chloride reaction for determining the presence of phenols and to the Fehling reaction for determining the presence of reducing sugars; gives positive results when subjected to the anisaldehyde-sulphuric acid reaction, the Molisch reaction with α-naphthol, the anthrone-sulphuric acid reaction, the tryptophane-sulphuric acid reaction, the chromotropic acid-sulphuric acid reaction, the aniline-hydrochloric acid reaction, the resorcinol-hydrochloric acid reaction, the carbazole-cysteine-sulphuric acid reaction, the Tollens reaction and the thioglycol-sulphuric acid reaction; shows only one spot at the anode side when subjected to electrophoresis in a 0.05 mol. sodium borate solution for 90 minutes using a cellulose acetate membrane at 20-25 V/cm; and shows no antimicrobial action to bacteria, fungi and yeasts such as *Staphylococus aureus, Escherichia coli, Bacillus subtilis, Aspergillus niger* and *Candida albicans.*

The present inventors have noted the fact that the polysaccharide and protein-bound polysaccharide having the function of BRM could exert a great influence to the immune system and, as a result of many studies, it has been found that a substance extracted from marine algae belonging to the classes Phaeophyceae, Rhodophyceae and Chlorophyceae has an inhibiting activity against adsorption of HIV on human-derived lymphocytes and a function to inhibit the activity of reverse transcriptase (RTase) which is an enzyme essential for the proliferation of HIV. The present invention has been attained on the basis of such finding.

SUMMARY OF THE INVENTION

In a first aspect of the present invention, there is provided polysaccharides produced from marine algae, having the following properties:

(a)
- (i) positive results when subjected to the α-naphthol-sulfuric acid reaction, indole-sulfuric acid reaction, anthrone-sulfuric acid reaction or phenol-sulfuric acid reaction, or
- (ii) positive results when subjected to the α-naphthol-sulfuric acid reaction, indole-sulfuric acid reaction, anthrone-sulfuric acid reaction or phenol-sulfuric acid and Lowry-Folin process or ninhydrin reaction after hydrochloric acid hydrolysis;

(b) an elementary analysis of 20-55% carbon, 3-9% hydrogen and less than 16 % nitrogen;

(c) a pH of 6.0-7.5;

(d) to contain as sugar component at least two kinds of saccharide selected from glucose, glucuronic acid, xylose and mannose and as protein component at least three kinds of amino acid selected from aspartic acid, lysine, leucine, glutamic acid and glycine;

(e)
- (i) absorption peaks at 3600-3200 cm$^{-1}$, or
- (ii) 3600-3200 cm$^{-1}$ and 1700-1600 cm$^{-1}$ in an infrared absorption spectrum;

(f) a molecular weight of $10^3 - 3 \times 10^6$ as measured by gel filtration chromatography; and (g) soluble in water and aqueous solvents containing water-soluble alcohols, acids or bases but insoluble in organic solvents of chloroform, benzene and ether.

In a second aspect of the present invention, there is provided an antiviral drug containing as an active ingredient an effective amount of polysaccharides extracted from marine algae.

DETAILED DESCRIPTION OF THE INVENTION

The characteristic of the present invention lies in polysaccharides extracted from marine algae and having an inhibiting activity against adsorption of HIV on human lymphocytes and a function to inhibit the RTase activity (said polysaccharides being hereinafter referred to as the present substance) and an antiviral drug containing the polysaccharides as active ingredient.

Marine algae are roughly classified into three classes: Phaeophyceae, Rhodophyceae and Chlorophyceae. The classification of the algae under consideration in the present invention conforms to Y. Yamada and S. Segawa: "An Illustrated Book of the Japanese Marine Algae" (published June 1, 1971, by Hoikusha) and its "Supplement" (published July 1, 1977) and T. Yamade et al: "Iwanami Encyclopedia Biologica" 3rd Ed. (published Mar. 10, 1983, by Iwanami Shoten).

The Phaeophyceae usable in the present invention include Ectocarpales, Sphacelariales, Cutleriales, Dictyotales, Chordariales, Sporochnales, Desmarestiales, Punctariales, Dictyosiphonales, Laminariales, and Fucales. The Rhodophyceae usable in the present invention include Porphyridiales, Goniotrichales, Bangiales, Compsopogonales (Protoflorideophyceae), and Nemaliales, Gelidiales, Cryptonemiales, Gigartinales, Rhodymeniales and Ceramiales (Florideophyceae). The Chlorophyceae usable in the present invention include Volvocales, Tetrasporales, Chlorococcales, Ulotrichales, Ulvales, Prasiolales, Sphaeropleales, Cladophorales, Siphonocladales, Oedogoniales, Dasycladales and Codiales.

Among the orders of algae, those belonging to the genera Nemacystus, Kjellmaniella, Laminaria, Undaria, Hizikia, Porphyra, Gelidium, Gloiopeltis, Gracilaria, Hemineura, Chlorella, Ulva, Spirogyra, Codium and Acetabularia are preferred.

The present substance can be obtained by extracting the marine algae with an aqueous solvent and subjecting the extract to refining treatment.

The aqueous solvent used for the extraction can be water or an aqueous solution containing a small quantity, for example not more than about 10% by weight of an organic solvent, acid, base or salt soluble in water. The extraction according to the present invention is carried out by the method selected from the group consisting of the water extraction, the organic-solvent extraction, the acid-solution extraction, the base-solution extraction, the salt-solution extraction and a combination thereof. The organic solvents usable in the above extraction include are methanol, ethanol, isopropyl alcohol and the like. The acids usable in the above extraction include hydro-chloric acid, sulfuric acid, acetic acid and the like. As the base, there can be used ammonia, sodium hydroxide, potassium hydroxide, sodium carbonate and the like. As the salt, sodium chloride, potassium chloride and the like can be used.

The extraction is carried out usually at a temperature from 4° to 120° C. for from 20 minutes to 20 hours by using 5 to 200 times as much amount of extracting solution as the starting material (on dry basis).

The refining treatment is intended to remove the low-molecular weight substances by applying such treatment as salting-out, dialysis, ultrafiltration, reverse osmosis, gel filtration, precipitation by use of an organic solvent, etc., or a combination of such treatments. Technologically, it is preferred to conduct either ultrafiltration, reverse osmosis, or a combination thereof, which are a membrane separation method under pressure. In some cases, such treatment may be conducted after salting-out.

The agents usable for such salting-out include ammonium sulfate, common salt (sodium chloride), potassium chloride, barium carbonate and the like, among which ammonium sulfate is preferred. After this salting-out treatment, it is necessary to carry out dialysis, ultrafiltration, gel filtration, reverse osmosis or a combination thereof.

Dialysis is usually carried out by using a semi-permeable membrane such as cellophane or collodion membrane.

Gel filtration is practiced by using a column packed with an adsorbent such as dextran or polyacrylamide gel. A filler commercially available under the trade name of Cephadex, Biogel, etc., is usually used.

Ultrafiltration and reverse osmosis are both a method for fractionation by using a membrane under pressure. Ultrafiltration is usually carried out under a pressure of 0.5 to 5 kg/cm$^2$ and reverse osmosis is usually carried out under a pressure of 20 to 35 kg/cm$^2$.

Precipitation by use of an organic solvent is usually effected by using methanol, ethanol, isopropanol, acetone or the like. If necessary, an ion exchange treatment may be combined with said operations.

After the refining treatment(s), the product is dehydrated by spray-drying, freeze-drying or other means and worked into a commercial product.

The present substance obtained by subjecting to the extraction by using water or the equeous solution containing a small amount of the organic solvent, acid or salt soluble in the water, and refining treatment is preferably further treated with an aqueous alkaline solution and as a result, the antiviral effect of this substance is surprisingly increased. Such aqueous alkaline solution treatment is accomplished, for example, by treating the present substance in a 0.01 to 5N, preferably 0.1 to 2N alkaline solution of an amount 5 to 200 times the starting material (on dry basis) at a temperature from 40° to 250° C., preferably from 60° to 200° C., more preferably from 100° to 150° C., for from 5 minutes to 2 hours, preferably from 10 minutes to one hour. Then, the treated solution is neutralized and subjected to refining treatment. Refining treatment is accomplished by applying the salting-out, dialysis, ultrafiltration, reverse osmosis, gel filtration, precipitation by use of an organic solvent or a combination thereof. The conditions to be used for such refining treatments are the same as described above. After this refining operation, the product is dehydrated by spray-drying, freeze-drying or other means.

The present substance obtained in the manner described above (i) gives positive results when subjected to the α-naphthol-sulfuric acid reaction, indole-sulfuric acid reaction, anthrone-sulfuric acid reaction or phenol-sulfuric acid reaction (polysaccharide), or (ii) gives positive results when subjected to the α-naphthol-sulfuric acid reaction, indole-sulfuric acid reaction, anthrone-sulfuric acid reaction or phenol-sulfuric acid reaction, and Lowry-Folin process or ninhydrin reaction after hydrochloric acid hydrolysis (protein-bound polysaccharide).

The elementary analysis of the present substance showed 20–55% carbon, 3–9% hydrogen and less than 16% nitrogen. The pH was 6.0 to 7.5.

The present substance contains as its sugar component at least two kinds of saccharide selected from glucose, glucuronic acid, xylose and mannose, and contains as its protein component at least three kinds of amino acid selected from aspartic acid, lysine, leucine, glutamic acid and glycine.

The infrared absorption spectrum of the present substance shows absorption of hydroxyl group in the region of 3600–3200 cm$^{-1}$ (polysaccharide), or shows absorption of hydroxyl group in the region of 3600–3200 cm$^{-1}$ and absorption attributable to amide group in the region of 1700–1600 cm$^{-1}$ (protein-bound polysaccharide).

The present substance is soluble in aqueous solvents and insoluble in organic solvents. The "aqueous solvents" mentioned above include water, and aqueous water-soluble alcohols, acids and bases, and the "organic solvents" include chloroform, benzene, ether and the like.

The present substance has a white, green or brown color and its molecular weight as determined by gel filtration chromatography is $10^3$ to $3 \times 10^6$.

In an acute toxicity test of the present substance, in which the present substance was administered at a dose of 1,000 mg/kg to the Donryu-strain rats which were 4 to 5 weeks old and weighed 100 to 150 grams, all of the rats were alive in the seven-day observation period after the administration.

The present substance is a safe material which is extremely low in its toxicity and causes almost no harmful side-effect.

It is known that generally a virus is adsorbed on a target cell and the nucleic acid of the virus is injected into the cell and integrated into the genome of the cell, and the virus is replicated after this process. In the case of retrovirus, before integration into the cell genome, there is required a process of transcription of RNA, which is the nucleic acid derived from the virus, into DNA by the action of a reverse transcriptase.

The present substance inhibits adsorption of HIV (human immunodeficiency virus) on human lymphocytes and succeeding infection thereof. It also inhibits the activity of reverse transcriptase. These effects of the present substance have been experimentally determined. For example, when the effect of the present substance was examined by a method in which HIV was treated with an algae extract of a concentration of 50-1,000 μg/ml at 0° C. for 2 hours, then washed and applied to a MT-4 cell to have it infected with HIV and after 3-day culture the HIV antigen positive cells were counted, it was found that the pre-treatment with the present substance had caused disappearance of substantially all of the HIV antigen positive cells, indicating the strong inhibiting activity of the present substance against adsorption of HIV on human lymphocytes. Also, when the influence of the present substance on the reverse transcriptase activity was examined by using whole messenger RNA from rat liver as template, a strong inhibition against reverse transcriptase activity was seen by the addition 50 to 1,000 μg/ml of the present substance.

These experimental results attest to the fact that the present substance has an inhibiting activity against viral infection, especially against the infection by retroviruses having reverse transcriptase, and is efficacious against the diseases caused by HIV infection, such as AIDS in particular.

In the case of AZT which is already in use as an antiviral drug, it produces a side effect detrimental to the normal cell division, whereas the present substance is a safe material which is extremely low in acute toxicity and useful as an antiviral agent since the present substance shows an inhibiting activity against viral infection, especially retroviral infection. Thus, the present substance is effective for the treatment of the viral infectious diseases, especially retroviral infectious diseases such as AIDS.

In use of the present substance as an antiviral drug, it can be offered in any desired form of preparation. Also, the drug can be administered in various ways. Further, the present substance can be used in combination with other known antiviral drugs such as AZT without lowering the normal efficacy. Such combined use is indeed an effective means for the treatment of the diseases.

In case the present substance is applied orally, it is worked into the form of tablet, granules, powder, capsule or like preparations which may contain in their composition an adjuvant or adjuvants which are normally used in the preparation of pharmaceuticals, such as binder, inclusion, excipient, lubricant, disintegrator, wetting agent, etc. In the case where the present substance is applied as a liquid preparation for oral administration, the preparation may take the form of liquid for internal use, shake mixture, suspension, emulsion, syrup or the like. It may take the form of a dry product which is turned into a liquid when used. These liquid preparations may contain the ordinarily used additives and preservatives. In the case of injection, the composition may contain such additives as stabilizer, buffering agent, preservative, isotonizing agent, etc., and is offered in the form of unit-dose ampule or in multiple-dose containers. The composition may take the form of aqueous solution, suspension, solution, emulsion in an oleaginous or aqueous vehicle, and the like. The active ingredient (the present substance) of such preparations may be a powder which, when used, is redissolved in a suitable vehicle such as pyrogen-free sterilized water.

The antiviral drug according to the present invention is administered to man and animals either orally or parenterally. Oral administration includes sublinqual application. Parenteral administration includes injection such as subcutaneous, intramuscular and intravenous injection and instillation. The dosage of the antiviral drug according to the present invention is variable depending on whether the subject is man or animal and according to such factors as age, individual differences, condition of the disease, etc., but usually in the case where the subject is man, the oral dose of the present substance is 0.1 to 1,000 mg, preferably 1 to 100 mg, per kg of body weight and day, and this amount of the substance is given in one to three portions.

The present substance is a material which is extremely low in acute toxicity and high in safety, and has an inhibiting activity against adsorption of HIV on human lymphocytes as well as a function to inhibit the activity of reverse transcriptase. Further, the present substance is a material useful for the treatment of viral infectious diseases, especially retroviral infectious diseases such as AIDS in particular.

The present invention is explained in more detail in the following Examples; however, it should be recognized that the scope of the present invention is not restricted to these Examples.

EXAMPLE 1

100 g of a dry Nemacystus decipines belonging to the genus Nemacystus of the family Spermatochnaceae of the order Chordariales in the Phaeophyceae was broken into fine chips, put into a 3-liter stainless steel tank, added with 2,000 ml of water and stirred while maintaining the temperature at 90°-95° C. The extraction was carried out for about 3 hours and then the resultant solution was cooled to room temperature.

The extract slurry was centrifuged to be separated into extract solution and residue. The residue was further extracted with 2,000 ml of 0.4N NaOH at 90°-95° C. for 3 hours, cooled to room temperature, adjusted to a pH of 7.0 with 2N HCl and centrifuged to be separated into extract solution and residue.

The extract solutions were joined, concentrated to 400 ml by a vacuum concentrator, desalted by using an ultrafilter and then dried by freeze drying to obtain 21 g of a dry product (A).

EXAMPLE 2

100 g of dry Kjellmaniella gyrate belonging to the genus Kjellmaniella of the family Laminariaceae of the order Laminariales in the Phaeophyceae were broken into chips, put into a 3-liter stainless steel tank, added with 2,000 ml of water and stirred with temperature kept at 90°–95° C. After about 3 hours of extraction, the resultant solution was cooled to room temperature.

The extract slurry was centrifuged to be separated into extract solution and residue. The residue was further extracted with 2,000 ml of 0.4N NaOH at 90°–95° C. for 3 hours, cooled to room temperature, adjusted to a pH of 7.0 with 2N HCl and centrifuged to be separated into extract solution and residue.

The extract solutions were joined, concentrated to 400 ml by a vacuum concentrator, desalted by using an ultrafilter and dried by freeze-drying to obtain 23 g of a dry product (B).

EXAMPLE 3

100 g of dry Laminaria japonica selected from the genus Laminaria of the family Laminariaceae of the order Laminariales in the Phaeophyceae were broken into fine chips, put into a 3-liter stainless steel tank, added with 2,000 ml of water and stirred with temperature kept at 90°–95° C. Extraction was carried out for about 3 hours, followed by cooling to room temperature.

The extract slurry was centrifuged to be separated into extract solution and residue. The residue was further extracted with 2,000 ml of 0.4N NaOH at 90°–95° C. for 3 hours and the resultant solution was cooled to room temperature, adjusted to a pH cf 7.0 with 2N HCl and then centrifuged to be separated into extract solution and residue.

The extract solutions were joined, concentrated to 400 ml by a vacuum concentrator, desalted by using an ultrafilter and dried by freeze drying to obtain 20 g of a dry product (C).

EXAMPLE 4

100 g of dry Undaria pinnatifida belonging to the genus Undaria of the family Laminariaceae of the order Laminariales in the Phaeophyceae was broken into fine chips, put into a 3-liter stainless steel tank, added with 2,000 ml of water and stirred while maintaining the temperature at 90°–95° C. The extraction was carried out for about 3 hours and then the resultant solution was cooled to room temperature.

The extract slurry was centrifuged to be separated into extract solution and residue, and the residue was further extracted with 2,000 ml of 0.4N NaOH at 90°–95° C. for 3 hours and the resultant solution was cooled to room temperature, adjusted to a pH of 7.0 with 2N HCl and centrifuged to be separated into extract solution and residue.

The extract solutions were joined, concentrated to 400 ml by a vacuum concentrator, desalted by using an ultrafilter and dried by freeze drying to obtain 18 g of a dry product (D).

EXAMPLE 5

100 g of dry Hizikia fusiforme belonging to the genus Hizikia of the family Sargassaceae of the order Fucales in the Phaeophyceae were broken into fine chips, put into a 3-liter stainless steel tank, added with 2,000 ml of water and stirred with temperature kept at 90°–95° C. The extraction was carried out for about 3 hours and then the resultant solution was cooled to room temperature.

The extract slurry was centrifuged to be separated into extract solution and residue.

The extract solution was concentrated to 400 ml by a vacuum concentrator and dried by freeze-drying to obtain 20 g of a dry product (E-1).

EXAMPLE 6

100 g of the safe dry Hizikia fusiforme as used in Example 5 were broken into fine chips, put into a 3-liter stainless steel tank, added with 2,000 ml of water and stirred with temperature kept at 90°–95° C. The extraction was carried out for about 3 hours and then the resultant solution was cooled to room temperature.

The extract slurry was centrifuged to be separated into extract solution and residue. The residue was further extracted with 2,000 ml of 0.4N NaOH at 90°–95° C. for 3 hours, cooled to room temperature, adjusted to a pH of 7.0 with 2N HCl and centrifuged to be separated into extract solution and residue.

The extract solutions were joined, concentrated to 400 ml by a vacuum concentrator, desalted by an ultrafilter and then dried by freeze drying to obtain 25 g of a dry product (E-2).

EXAMPLE 7

20 g of the extract of Hizikia fusiforme obtained in Example 5 was dissolved in a 1N NaOH solution and subjected to a heat treatment at 120° C. for 20 minutes. After cooled to room temperature, the treated solution was adjusted to a pH of 7.0 with 2N HCl, desalted by using an ultrafilter and dried by freeze drying to obtain 19 g of an alkali treated product (E-3).

EXAMPLE 8

100 g of dry Porphyra tenera of the family Bangiaceae of the order Bangiales in the Rhodophyceae was broken into fine chips, put into a 3-liter stainless steel tank, added with 2,000 ml of distilled water and stirred while maintaining the temperature at 90°–95° C. After about 3 hours of extraction, the resultant solution was cooled to room temperature.

The extract slurry was centrifuged to be separated into extract solution and residue, and the residue was further extracted with 2,000 ml of 0.4N NaOH at 90°–95° C. for 3 hours and the resultant solution was cooled to room temperature, adjusted to a pH of 7.0 with 2N HCl and then centrifuged to be separated into extract solution and residue.

The extract solutions were joined, concentrated under reduced pressure, desalted by ultrafiltration and dried by freeze drying to obtain 30 g of a dry product (F).

EXAMPLE 9

100 g of dry Gelidium amansii belonging to the family Gelidiaceae of the order Gelidiales in the Rhodophyceae was broken into fine chips, put into a 3-liter stainless steel tank, added with 2,000 ml of distilled water and stirred while maintaining the temperature at 90°–95° C. The extraction was carried out for about 3 hours and then the resultant solution was cooled to room temperature.

The extract slurry was centrifuged to be separated into extract solution and residue. The residue was further extracted with 2,000 ml of 0.4N NaOH at 90°–95° C. for 3 hours and the extract was cooled to room temperature, adjusted to a pH of 7.0 with 2N HCl and centrifuged into extract solution and residue.

The extract solutions were joined, concentrated under reduced pressure, desalted by ultrafiltration and dried by freeze-drying to obtain 25 g of a dry product (G).

EXAMPLE 10

100 g of dry Gloiopeltis complanate belonging to the family Endocladiaceae of the order Cryptonemiales in the Rhodophyceae was broken into fine chips, put into a 3-liter stainless steel tank, added with 2,000 ml of distilled water with temperature kept at 90°–95° C. The extraction was carried out for about 3 hours and then the resultant solution was cooled to room temperature.

The extract slurry was centrifuged to be separated into extract solution and residue. The residue was further extracted with 2,000 ml of 0.4N NaOH at 90°–95° C. for 3 hours, cooled to room temperature, adjusted to a pH of 7.0 with 2N HCl and centrifuged into extract solution and residue.

The extract solutions were joined, concentrated under reduced pressure, desalted by ultrafiltration and dried by freeze-drying to obtain 27 g of a dry product (H).

EXAMPLE 11

100 g of dry Gracilaria rerrucosa belonging to the genus Gracilaria of the family Gracilariceae of the order Gigartinales in the Rhodophyceae was broken into fine chips, put into a 3-liter stainless steel tank, added with 2,000 ml of distilled water with temperature kept at 90°–95° C. The extraction was carried out for about 3 hours and then the resultant solution was cooled to room temperature.

The extract slurry was centrifuged into extract solution and residue, and the residue was further extracted with 2,000 ml of 0.4N NaOH at 90°–95° C. for 3 hours, cooled to room temperature, adjusted to a pH of 7.0 with 2N HCl and centrifuged into extract solution and residue.

The extract solutions were joined, concentrated under reduced pressure, desalted by ultrafiltration and dried by freeze drying to obtain 23 g of a dry product (I).

EXAMPLE 12

100 g of Hemineura schmitziana belonging to the genus Hemineura of the family Delesseriaceae of the order Ceramiales in the Rhodophyceae was crushed into fine chips, put into a 3-liter stainless steel tank, added with 2,000 ml of distilled water and stirred with temperature kept at 90°–95° C. The extraction was carried out for about 3 hours and then the resultant solution was cooled to room temperature.

The extract slurry was centrifuged into extract solution and residue, and the residue was further extracted with 2,000 ml of 0.4N NaOH at 90°–95° C. for 3 hours, then cooled to room temperature, adjusted to a pH of 7.0 with 2N HCl and centrifuged into extract solution and residue.

The extract solutions were joined, concentrated under reduced pressure, desalted by ultrafiltration and dried by freeze drying to obtain 22 g of a dry product (J).

EXAMPLE 13

100 g of pulverized Chlorella vulgaris belonging to the family Chlorellaceae of the order Chlorococcales was put into a 3-liter stainless steel tank, added with 2,000 ml of water with temperature kept at 90°–95° C. The extraction was carried out for about 3 hours and then the resultant solution was cooled to room temperature.

The extract slurry was centrifuged into extract solution and residue. The residue was further extracted with 2,000 ml of 0.4N NaOH at 90°–95° C. for 3 hours and the extract was cooled to room temperature, adjusted to a pH of 7.0 with 2N HCl and centrifuged into extract solution and residue.

The extract solutions were joined, concentrated to 400 ml by a vacuum concentrator, desalted by ultra-filtration and dried by freeze drying to obtain 13 g of a dry product (K-1).

EXAMPLE 14

100 g of finely divided Chlorella ellipsoidea powder was put into a 3-liter stainless steel tank, added with an aqueous solution of 0.4N NaOH and kept at 90°–95° C. while stirring the solution. The extraction was carried out for about 3 hours and then the resultant solution was cooled to room temperature. The extract was adjusted to a pH of 7.0 with 2N HCl and then centrifuged into extract solution and residue. The extract solution was concentrated to 400 ml by a vacuum concentrator, desalted by using an ultrafilter and then dried by freeze-drying to obtain about 12 g of a dry product (K-2).

EXAMPLE 15

100 g of pulverized Chlorella vulgaris was put into a 3-liter stainless steel tank, added with 2,000 ml of water and kept at 90°–95° C. under stirring. The extraction was carried out for about 3 hours and then the resultant solution was cooled to room temperature.

The extract slurry was centrifuged into extract solution and residue.

The extract solutions were joined, concentrated to 400 ml by a vacuum concentrator, desalted by ultra-filtration and dried by freeze-drying to obtain 10 g of a dry product (K-3).

EXAMPLE 16

100 g of pulverized ulra pertusa belonging to the family Ulvaceae of the order Ulvales in the Chlorophyceae was put into a 3-liter stainless steel tank, added with 1,000 ml of water and stirred while maintaining the temperature at 90°–95° C. The extraction was carried out for about 3 hours and then the resultant solution was cooled to room temperature.

The extract slurry was centrifuged into extract solution and residue. The residue was further extracted with 1,000 ml of 0.4N NaOH at 90°–95° C. for 3 hours and the extract was cooled to room temperature, adjusted to a pH of 7.0 with 2N HCl and centrifuged into extract solution and residue.

The extract solutions were joined, concentrated to 400 ml by a vacuum concentrator, desalted by ultra-filtration and dried by freeze drying to obtain 18 g of a dry product (L).

EXAMPLE 17

100 g of pulverized Spirogyra arcta belonging to the order Zygnematales in the Chlorophyceae was put into a 3-liter stainless steel tank, added with 1,000 ml of water and stirred with the temperature kept at 90°–95° C. After about 3-hour extraction, the resultant solution was cooled to room temperature.

The extract slurry was centrifuged into extract solution and residue, and the residue was further concentrated with 1,000 ml of 0.4N NaOH at 90°–95° C. for 3 hours, cooled to room temperature, adjusted to a pH of 7.0 with 2N HCl and centrifuged into extract solution and residue.

The extract solutions were joined, concentrated to 400 ml by a vacuum concentrator, desalted by ultra-filtration and dried by freeze-drying to obtain 15 g of a dry product (M).

EXAMPLE 18

100 g of pulverized Codium fragile of the order Codiales in the Chlorophyceae was put into a 3-liter stainless steel tank, added with 2,000 ml of water and stirred while maintaining the temperature at 90°-95° C. The extraction was carried out for about 3 hours and then the resultant solution was cooled to room temperature.

The extract slurry was centrifuged into extract solution and residue. The residue was further extracted with 2,000 ml of 0.4N NaOH at 90°-95° C. for 3 hours cooled to room temperature, adjusted to a pH of 7.0 with 2N HCl and centrifuged into extract solution and residue.

The extract solutions were joined, concentrated to 400 ml by a vacuum concentrator, desalted by ultra-filtration and dried by freeze-drying to obtain 17 g of a dry product (N).

EXAMPLE 19

100 g of powder of Acetabularia ryukyuensis was put into a 3-liter stainless steel tank, added with 2,000 ml of water and stirred by maintaining the temperature of 90°-95° C. The extraction was carried out for about 3 hours and then the resultant solution was cooled to room temperature.

The extract slurry was centrifuged into extract solution and residue. The residue was further extracted with 2,000 ml of 0.4N NaOH at 90°-95° C. for 3 hours, cooled to room temperature, adjusted to a pH of 7.0 with 2N HCl and centrifuged into extract solution and residue.

The extract solutions were joined, concentrated to 400 ml by a vacuum concentrator, desalted by ultra-filtration and dried by freeze drying to obtain 19 g of a dry product (O).

The physicochemical properties of the present substance extracted from the marine algae are shown in Table 1. In the table, the positive result of the phenol-sulfuric acid color reaction indicates the presence of saccharide, and the positive result of the Lowry-Folin color reaction indicates the presence of peptide bond. As for the molecular weight, the molecular weight distribution in the fraction rich with the present substance was determined by a gel filtration method and shown in the table.

EXAMPLE 20

The inhibiting effect of the present substances obtained in Examples 1-19 against reverse transcriptase specifically retained by retroviruses was determined by the following method.

10 mg of each of the present substances in the form of freeze-dried products (A)-(O) was dissolved in 10 ml of sterilized distilled water (concentration: 1 mg/ml).

1 $\mu$l of 20 mM D.T.T. (dithiothreitol, produced by Sigma Co., Ltd.), 5 $\mu$l of a 5-fold concentrated enzyme reaction solution (comprising 250 mM tris-HCl (pH 8.3), 250 mM KCl and 40 mM MgCl$_2$), 1 $\mu$l of 3d NTP solution (comprising 1 mM dATP, 1 mM GTP and 1 mM dTTP, produced by Sigma Co., Ltd.), 2 $\mu$l of 100 $\mu$g/ml oligomer (dt)$_{12-18}$ (produced by PL Biochemicals Co., Ltd.), 1 $\mu$l of messenger RNA (derived from normal rat liver; 1 $\mu$g/$\mu$l), 0.5 $\mu$l of RNase inhibitor (16 unit/$\mu$l, produced by Takara Shuzo Kabushiki Kaisha and 1 $\mu$l of [$\alpha$-$^{32}$p] dCTP (up to 800 Ci/mmol, 10 $\mu$Ci/$\mu$l, produced by Amersham Japan Co. Ltd.) were added into a 1.5 ml Eppendolf's tube and the Eppendolf's tube was placed in a 37° C. water bath.

5 minutes thereafter, 12.5 $\mu$l of each of the previously prepared solutions of the present substances (concentration: 1 mg/ml) was added into the reaction tube, followed by further addition of 1 $\mu$l of reverse transcriptase (7 unit/$\mu$l, derived from Rous associated virus, produced by Takara Shuzo Kabushiki Kaisha) so that the amount of the final reaction solution would become 25 $\mu$l, and the mixture was reacted at 37° C.

One hour thereafter, 5 $\mu$l of the reaction solution was infiltrated into the 2 cm$\times$2 cm sheets of DEAE paper (made by Toyo Roshi Kabushiki Kaisha), and after air-dried, each sheet was immersed in 10 ml of a 0.5 M aqueous solution of Na$_2$HPO$_4$ and [$\alpha$-$^{32}$p] dCTP not used for DNA synthesis and remaining on filter paper was washed away under shaking. (This operation was conducted 5 times at a five minutes' interval).

Thereafter, each of said DEAE paper sheets was placed in a glass vial containing 10 ml of a liquid scintillation cocktail (made bl, Axersham Japan Co., Ltd.) and the radioactivity of each sheet was counted for one minute (c.p.m.) by a scintillation counter(made by Aroka Co., Ltd.).

The reverse transcriptase activity inhibition rate (%) was determined from the following formula:

$$\text{Reverse transcriptase activity inhibition rate (\%)} = \frac{C_o - C_s}{C_o} \times 100$$

Co: Radioactivity of the sheet when not added with the present substance

Cs: Radioactivity of the sheet when added with the present substance

The reverse transcriptase (RTase) activity inhibition rates of the substances tested are shown in Table 1.

EXAMPLE 21

The inhibiting activity of the present substances against adsorption of HIV (AIDS virus) on human lymphocytes was determined by the following method. (All the operations were conducted under an aseptic condition).

1 ml of a suspension of HIV (human immunodeficiency virus) and 1 ml of an aqueous solution of present substance (800 $\mu$g/ml) were put into a test tube and the test tube was placed still in ice. Two hours thereafter, 1 ml of virus suspension was sampled out from the test tube and the virus was adsorbed on a cell strain MT-4 derived from human lymphocyte (Jpn. J. Cancer Res. (Gann), 28, 219-229 (1982)) at a multiplicity of infection (M.O.I.) $\simeq$2. After centrifuging at 2,000 r.p.m. for 10 minutes, the supernatant was eliminated and the sedimentary MT-4 cells were set force in RPMI 1640 containing 20% of FCS (Gibco Laboratories, NY) so that the cell concentration would become 2$\times$10$^5$ cell/ml.

100 $\mu$l portions of said MT-4 cell suspension were pipetted into the 96-hole plates and cultured under the conditions of 5% CO and 37° C. On the third day of culture, the number of the HIV adsorbed cells and the number of the non-adsorbed cells were calculated by using the indirect fluorescent antibody technique.

The HIV adsorption inhibition rate (%) was calculated from the following formula:

HIV adsorption inhibition rate (%) =

$$\frac{\text{HIV adsorbed cells}}{\text{HIV adsorbed cells + HIV non-adsorbed cells}} \times 100$$

The results are shown in Table 1.

PREPARATION EXAMPLE 330 mg of the present substance of Example 1 was filled in each of the #0 hard capsules by using a pressure type automatic filler to prepare the capsules containing the present substance.

TABLE 1

| Physico-chemical of extract | Present substance | | | | | | |
|---|---|---|---|---|---|---|---|
| | Compound of Example 1 A | Compound of Example 2 B | Compound of Example 3 C | Compound of Example 4 D | Compound of Example 5 E-1 | Compound of Example 6 E-2 | Compound of Example 7 E-3 |
| Material (Genus) | Nemacystus | Kjellmaniella | Laminaria | Undaria | Hizikia | Hizikia | Hizikia |
| Color material | Light brown | Light brown | Light brown | Light brown | Light brown | Light brown | Light brown |
| pH | 6.7 | 6.7 | 6.1 | 6.2 | 6.0 | 6.2 | 6.9 |
| Absorption in infrared region ($cm^{-1}$) | 3600–3200 1700–1600 | 3600–3200 1700–1600 | 3600–3200 1700–1600 | 3600–3200 1700–1600 | 3600–3200 1700–1600 | 3600–3200 1700–1600 | 3600–3200 1700–1600 |
| Phenol-sulfuric acid color reaction | + | + | + | + | + | + | + |
| Lowry-Folin color reaction | + | + | + | + | + | + | + |
| Molecular weight distribution | 10,000–200,000 | 10,000–200,000 | 10,000–200,000 | 10,000–200,000 | 10,000–200,000 | 10,000–200,000 | 10,000–200,000 |
| Solubility | soluble in water | soluble in water | soluble in water | soluble in water | soluble in water | soluble in water | soluble in water |
| Elementary analysis | C: 26.5 H: 3.6 N: 4.0 | C: 35.0 H: 5.0 N: 3.3 | C: 33.0 H: 4.6 N: 2.0 | C: 41.0 H: 6.0 N: 3.5 | C: 30.1 H: 4.6 N: 1.0 | C: 31.6 H: 4.2 N: 1.1 | C: 29.8 H: 4.5 N: 0.9 |
| Solubility in chloroform | insoluble | insoluble | insoluble | insoluble | insoluble | insoluble | insoluble |
| RTase activity inhibition rate (%)* | +++ | +++ | +++ | +++ | ++ | +++ | +++ |
| HIV adsorption inhibition rate (%)* | +++ | +++ | +++ | +++ | ++ | +++ | +++ |
| Protein content (%) | 26.5 | 20.2 | 11.5 | 23.0 | 5.2 | 4.8 | 6.2 |
| Sugar Content (%) | 51.3 | 63.3 | 67.2 | 72.5 | 90.3 | 88.1 | 80.5 |

| Physico-chemical of extract | Present substance | | | | | | |
|---|---|---|---|---|---|---|---|
| | Compound of Example 8 F | Compound of Example 9 G | Compound of Example 10 H | Compound of Example 11 I | Compound of Example 12 J | Compound of Example 13 K-1 | Compound of Example 14 K-2 |
| Material (Genus) | Porphyra | Gelidium | Gloriopeltis | Gracilaria | Hemineura | Chlorella | Chlorella |
| Color material | Light brown | Light brown | Light brown | Light brown | Light brown | Light brown | Light brown |
| pH | 6.4 | 6.0 | 6.5 | 6.3 | 6.9 | 7.2 | 6.5 |
| Absorption in infrared region ($cm^{-1}$) | 3600–3200 1700–1600 | 3600–3200 1700–1600 | 3600–3200 1700–1600 | 3600–3200 1700–1600 | 3600–3200 1700–1600 | 3600–3200 1700–1600 | 3600–3200 1700–1600 |
| Phenol-sulfuric acid color reaction | + | + | + | + | + | + | + |
| Lowry-Folin color reaction | + | + | + | + | + | + | + |
| Molecular weight distribution | 10,000–200,000 | 10,000–200,000 | 10,000–200,000 | 10,000–200,000 | 10,000–200,000 | 10,000–200,000 | 10,000–200,000 |
| Solubility | soluble in water | soluble in water | soluble in water | soluble in water | soluble in water | soluble in water | soluble in water |
| Elementary analysis | C: 46.0 H: 6.2 N: 7.6 | C: 45.4 H: 6.5 N: 0.3 | C: 41.8 H: 6.0 N: 6.5 | C: 42.5 H: 5.8 N: 5.1 | C: 43.8 H: 6.1 N: 4.0 | C: 24.6 H: 5.1 N: 12.5 | C: 31.2 H: 4.8 N: 9.0 |
| Solubility in chloroform | insoluble | insoluble | insoluble | insoluble | insoluble | insoluble | insoluble |
| RTase | ++ | +++ | ++ | ++ | ++ | +++ | +++ |

TABLE 1-continued

| | Compound of Example 8 | Compound of Example 9 | Compound of Example 10 | Compound of Example 11 | Compound of Example 12 | Compound of Example 13 | Compound of Example 14 |
|---|---|---|---|---|---|---|---|
| activity inhibition rate (%)* | | | | | | | |
| HIV adsorption inhibition rate (%)* | +++ | +++ | + | ++ | + | +++ | +++ |
| Protein content (%) | 45.0 | 2.3 | 37.8 | 31.2 | 26.3 | 76.8 | 53.0 |
| Sugar content (%) | 42.3 | 83.5 | 40.3 | 54.4 | 63.5 | 8.3 | 12.5 |

| Physico-chemical of extract | Present substance | | | | |
|---|---|---|---|---|---|
| | Compound of Example 15 K-3 | Compound of Example 16 L | Compound of Example 17 M | Compound of Example 18 N | Compound of Example 19 O |
| Material (Genus) | Chlorella | Ulva | Spirogyra | Codium | Acetabularia |
| Color material | Light brown | Light brown | Light brown | Light brown | Light brown |
| pH | 6.0 | 7.3 | 6.8 | 6.2 | 7.0 |
| Absorption in infrared region ($cm^{-1}$) | 3600–3200 1700–1600 | 3600–3200 1700–1600 | 3600–3200 1700–1600 | 3600–3200 1700–1600 | 3600–3200 1700–1600 |
| Phenol-sulfuric acid color reaction | + | + | + | + | + |
| Lowry-Folin color reaction | + | + | + | + | + |
| Molecular weight distribution | 10,000–200,000 | 10,000–200,000 | 10,000–200,000 | 10,000–200,000 | 10,000–200,000 |
| Solubility | soluble in water | soluble in water | soluble in water | soluble in water | soluble in water |
| Elementary analysis | C: 29.8 H: 4.4 N: 14.0 | C: 29.4 H: 3.8 N: 1.8 | C: 30.1 H: 4.8 N: 3.4 | C: 35.0 H: 4.4 N: 2.8 | C: 42.6 H: 5.5 N: 4.8 |
| Solubility in chloroform | insoluble | insoluble | insoluble | insoluble | insoluble |
| RTase activity inhibition rate (%)* | ++ | ++ | ++ | +++ | +++ |
| HIV adsorption inhibition rate (%)* | +++ | +++ | +++ | +++ | +++ |
| Protein content (%) | 88.0 | 13.0 | 21.0 | 17.2 | 36.3 |
| Sugar Content (%) | 6.3 | 60.2 | 68.5 | 72.2 | 54.8 |

*(Note)
+++: 70–100%
++: 30–69%
+: 0–29%

What is claimed is:

1. A protein-bound polysaccharide, having antiviral activity, obtained from a marine alga belonging to the genera Nemacystus, Kjellmaniella, Laminaria, Undaria, Hizikia, Porphyra, Gelidium, Gloiopeltis, Gracilaria, Hemineura, Ulva, Spirogyra, Codium and Acetabularia having the following properties:

(a) positive results when subjected to the α-naphthol-sulfuric acid, indole-sulfuric acid, anthrone-sulfuric acid or phenol-sulfuric acid reaction and, after hydrochloric acid hydrolysis, a Lowry-Folin process or ninhydrin reaction;

(b) elementary analysis: 20–55% carbon, 3–9% hydrogen and less than 16% nitrogen;

(c) a pH of 6.0–7.5;

(d) the sugar component comprises at least two kinds of saccharides selected from glucose, glucuronic acid, xylose and mannose, and the protein component comprises at least three kinds of amino acids selected from aspartic acid, lysine, leucine, glutamic acid and glycine;

(e) infrared absorption spectrum peaks at 3,600-3,200 $cm^{-1}$ and 1,700-1,600 $cm^{-1}$;

(f) a molecular weight of $10^3$-$3 \times 10^6$ as measured by gel filtration chromatography; and (g) soluble in water or aqueous solvents containing water-soluble alcohols, acids or bases but insoluble in chloroform, benzene and ether.

2. A protein-bound polysaccharide according to claim 1, which is obtained by extracting said marine alga with an aqueous solvent and thereafter refining the extract.

3. The protein-bound polysaccharide according to claim 2, wherein said aqueous solvent is water or an aqueous solution in which a water-soluble organic solvent, acid base or salt is dissolved.

4. The protein-bound polysaccharide according to claim 2, wherein said extraction is carried out at 4°–120°

C. for 20 minutes to 20 hours using 5 to 200 times the amount of extracting solution as said marine alga on a dry basis.

5. The protein-bound polysaccharide according to claim 2, wherein said refining is by salting-out, dialysis, ultrafiltration, reverse osmosis, gel filtration or precipitation by an organic solvent.

6. The protein-bound polysaccharide according to claim 2, wherein said aqueous solution of solvent is an aqueous ammonia, sodium hydroxide, potassium hydroxide or sodium carbonate.

7. A pharmaceutical composition comprising, together with a pharmaceutically acceptable carrier or diluent, as an active ingredient, an effective amount of an antiviral protein-bound polysaccharide extracted from a marine alga belonging to genera Nemacystus, Kjellmaniella, Laminaria, Undaria, Hizikia, Porphyra, Gelidium, Gloiopeltis, Gracilaria, Hemineura, Ulva, Spirogyra, Codium and Acetabularia, said protein-bound polysaccharide having the following properties:

(a) positive results when subjected to the α-naphthol-sulfuric acid, indole-sulfuric acid, anthrone-sulfuric acid or phenol-sulfuric acid reaction and, after hydrochloric acid hydrolysis, a Lowry-Folin process or ninhydrin reaction;

(b) elementary analysis: 20-55% carbon, 3-9% hydrogen and less than 16% nitrogen;

(c) a pH of 6.0-7.5;

(d) the sugar component comprises at least two kinds of saccharides selected from glucose, glucuronic acid, xylose and mannose, and the protein component comprises at least three kinds of amino acids selected from aspartic acid, lysine, leucine, glutamic acid and glycine;

(e) infrared absorption spectrum peaks at 3,600-3,200 $cm^{-1}$ and 1,700-1,600 $cm^{-1}$;

(f) a molecular weight of $10^3 - 3 \times 10^6$ as measured by gel filtration chromatography; and (g) soluble in water or aqueous solvents containing water-soluble alcohols, acids or basis but insoluble in chloroform, benzene and ether.

8. The pharmaceutical composition according to claim 7, wherein the polysccharide is obtained by extracting the marine algae with an aqueous solvent and subjecting the extract to refining treatment.

9. The pharmaceutical composition according to claim 8, wherein said aqueous solvent is water or an aqueous solution in which a water-soluble organic solvent, acid, base or salt is dissolved.

10. The pharmaceutical composition according to claim 8, wherein said extraction is carried out at 4°-120° C. for 20 minutes to 20 hours using 5 to 200 times the amount of extracting solution as said marine alga on a dry basis.

11. The pharmaceutical composition according to claim 8, wherein the refining is by salting-out, dialysis, ultrafiltration, reverse osmosis, gel filtration or precipitation by an organic solvent.

12. The pharmaceutical composition according to claim 9, wherein said aqueous solution of solvent is a solution of aqueous ammonia, sodium hydroxide, potassium hydroxide or a sodium carbonate.

13. The pharmaceutical composition according to claim 7, wherein asid protein-bound polysaccharide is obtained by extracting said marine alga with water or an aqueous solution of a water-soluble organic solvent, acid or salt; refining the extract; further treating the refined material with 5 to 200 times the amount of a 0.01-5N aqueous alkaline solution as said marine alga on a dry basis at 40°-250° C. for 5 minutes to 2 hours; and refining the resulting material.

14. The pharmaceutical composition of claim 7 for treating retroviral infections.

* * * * *

UNITED STATES PATENT AND TRADEMARK OFFICE
CERTIFICATE OF CORRECTION

PATENT NO. : 5,089,481
DATED : February 18, 1992
INVENTOR(S) : MUTO et al

It is certified that error appears in the above-indentified patent and that said Letters Patent is hereby corrected as shown below:

On the title page, item [30], Foreign Application Priority Data fourth line, should read
--Jun. 18, 1987 [JP] Japan ....62-152088--

Signed and Sealed this

Twenty-ninth Day of March, 1994

Attest:

BRUCE LEHMAN

Attesting Officer           Commissioner of Patents and Trademarks